United States Patent
Morris et al.

(10) Patent No.: US 8,007,103 B2
(45) Date of Patent: Aug. 30, 2011

(54) SYSTEM AND METHOD FOR PRESCRIPTION OF VISUAL AIDS

(75) Inventors: Michael Morris, Petaluma, CA (US); Jesus Miguel Guillen Cabeza, Aalen (DE); Timo Kratzer, Aalen (DE)

(73) Assignee: Carl Zeiss Vision GmbH, Aalen (DE)

( * ) Notice: Subject to any disclaimer, the term of this patent is extended or adjusted under 35 U.S.C. 154(b) by 362 days.

(21) Appl. No.: 12/192,463

(22) Filed: Aug. 15, 2008

(65) Prior Publication Data

US 2010/0039614 A1 Feb. 18, 2010

(51) Int. Cl.
*A61B 3/00* (2006.01)
*A61B 3/10* (2006.01)
*A61B 3/14* (2006.01)

(52) U.S. Cl. .................. 351/200; 351/205; 351/206

(58) Field of Classification Search .............. 351/200, 351/206, 222, 245
See application file for complete search history.

(56) References Cited

U.S. PATENT DOCUMENTS

| | | | |
|---|---|---|---|
| 6,382,795 B1 | 5/2002 | Lai | |
| 2002/0140902 A1 | 10/2002 | Williams | |
| 2007/0109498 A1 | 5/2007 | Lai et al. | |
| 2007/0115432 A1 | 5/2007 | Thibos | |
| 2008/0129962 A1 | 6/2008 | Dai | |
| 2009/0015787 A1* | 1/2009 | Guillen et al. | 351/205 |

FOREIGN PATENT DOCUMENTS

| | | |
|---|---|---|
| DE | 601 21 123 T2 | 2/2007 |
| WO | WO/2004 096014 | 11/2004 |

OTHER PUBLICATIONS

U.S. Appl. No. 11/840,688, filed Aug. 17, 2007, Jesus Miguel Guillen Cabeza.

* cited by examiner

*Primary Examiner* — Ricky Mack
*Assistant Examiner* — Brandi N Thomas
(74) *Attorney, Agent, or Firm* — Fish & Richardson P.C.

(57) ABSTRACT

In one aspect, the invention features a method for determining an eyeglass prescription for an eye. The method includes obtaining a measurement of a wavefront indicative of the refractive properties of the eye, establishing an optimization space corresponding to a plurality of possible prescriptions for the eye, determining a value for a merit function for each of the possible prescriptions in the optimization space, where the merit function value corresponds to a visual function of the eye when corrected using the corresponding possible prescription, generating a representation of the merit function values, and outputting the representation to an eye care professional.

27 Claims, 4 Drawing Sheets

SYSTEM AND METHOD FOR PRESCRIPTION OF VISUAL AIDS

BACKGROUND

The disclosure relates to systems and methods for determining a prescription of visual aids.

The ametropic human eye has refractive errors that in first approximation can be described in terms of a sphere, a cylinder and an axis orientation. This is based on the assumption that the visual defect can be approximately corrected through a lens with simple surfaces such as toroids and spheres. This approximation is adequate to correct an error in the refraction of light rays that enter the center of the eye pupil.

While it is customary to determine the refractive errors of the human eye by relying on the subjective refraction of the patient under examination when presenting to him a plurality of optotypes through lenses of different refractive power (subjective or manifest refraction), the possibility of measuring the refractive errors of the eye has now been available for several years (objective refraction). Moreover, it is possible to measure the refractive power of the eye over the entire pupil and in particular also in the peripheral areas of the pupil. The measurable errors include for example spherical aberration, coma, trefoil error, higher orders of spherical aberration, etc. In certain implementations, the objective refraction method is based on determining the wavefront of a propagating light bundle. The functional principal of a wavefront refractor is described in DE 601 21 123 T2, which also includes a synopsis of a plurality of different variants.

The refractive errors or imaging errors of the human eye can also be described by means of so-called Zernike polynomials. The errors of the eye near the center of the pupil in regard to sphere, cylinder and axis can be described, for example, through second-order Zernike polynomials. These errors are therefore often referred to as second-order errors. The errors far from the center can be described through higher-order Zernike polynomials. These errors are therefore in general also referred to as higher-order errors.

The information gained from a wavefront refractor can be used in the development of improved vision aids or improved eyesight correction methods. A well-known example for an eyesight correction method is the procedure of wavefront-guided refractive surgery. In this procedure, a volume of any desired geometry is removed from the surface of the cornea in order to correct refractive errors, including those of a higher order.

SUMMARY

In general, in order to determine a prescription for visual aids, an eye care professional determines several parameters. In the case of spectacle lenses, for example, the most relevant ones are: refractive values, usually given in form of sphere, cylinder and axis; fitting parameters, such as pupil distance, fitting height, pantoscopic angle and others; and near vision addition, for example, in the case of progressive lenses. For contact lenses, the set of parameters usually includes at least the refractive values, similar to spectacle lenses, and corneal curvature.

Conventionally, the determination of refractive values involves the use of manifest refraction techniques. Typically, this is performed by first establishing a first set of (sphere, cylinder, axis) values as starting point for an optimization. The starting point can be obtained, e.g., through retinoscopy, an autorefractor measurement, through measurement of the currently worn spectacle lenses, or other methods. Then, an iterative optimization process is started, in which different refractive corrections, i.e., sets of (sphere, cylinder, axis) values are offered to the patient, until he/she achieves a maximum of visual acuity on an eye chart.

Although newer, advanced objective refraction techniques are available, they have not achieved widespread adoption because many eye care professionals are reluctant to change from the tried and trusted manifest refraction, and also because objective refraction techniques don't necessarily provide allowance for consideration of a variety of factors that may make a certain prescription more desirable for a patient that the prescription corresponding to the global maximum provided by an objective refraction. As an example, a prescription that leaves the cylinder axis value unchanged from a previous prescription may be preferred over a global maximum prescription that requires a change in cylinder axis.

The disclosure features methods for determining refractive values for a patient's eyeglass prescription that utilize objective refraction but also allow an eye care professional to consider other factors. For example, in certain embodiments, the methods provide guidance to an eye care professional in the optimization strategy of manifest refraction to reach a global maximum for visual acuity in a reliable way based on the measurement of higher order aberrations of the eye using an aberrometer.

In one aspect, the invention features a method for determining an eyeglass prescription for an eye. The method includes obtaining a measurement of a wavefront indicative of the refractive properties of the eye, establishing an optimization space corresponding to a plurality of possible prescriptions for the eye, determining a value for a merit function for each of the possible prescriptions in the optimization space, where the merit function value corresponds to a visual function of the eye when corrected using the corresponding possible prescription, generating a representation of the merit function values, and outputting the representation to an eye care professional.

Implementations of the method can include one or more of the following features and/or features of other aspects. For example, establishing the optimization space can include defining ranges for one or more parameters characterizing the prescription. The one or more parameters characterizing the prescription can include one or more of the following: sphere, cylinder, axis, M, J0, and J45.

The optimization space can be a single space, such as, for example, a space having three or more dimensions. The or more dimensions can include sphere, cylinder, and axis or M, J0, and J45. In some embodiments, the optimization space comprises two or more sub-spaces One of the subspaces can include a dimension for sphere. Another one of the subspaces can include a dimension for cylinder and a dimension for axis. In certain embodiments, one of the subspaces can include a dimension for M and another one of the subspaces includes a dimensions for J0 and a dimension for J45.

Determining the value for the merit function can include determining a plurality of corrected wavefronts each indicative of the refractive properties of the eye and the corresponding possible prescription.

The representation can be a graphical representation.

The representation can be output so that the eye care professional can identify a prescription corresponding to a maximum merit function value from the representation. In some embodiments, the representation is output so that the eye care professional can identify one or more prescriptions corresponding to prescriptions at which vision becomes blurred. The representation can be output so that the eye care professional can identify one or more prescriptions that correspond to prescriptions having a relatively small value for cylinder, having the cylinder axis relatively close to 0° or 90°, having a relatively large plus mean spherical power, corresponding to a relatively light ophthalmic lens, giving a relatively small distortion on a particular ophthalmic lens design, corresponding to a small ablation depth for refractive surgery, and/or being relatively close to certain pre-established values.

The representation can include one or more plots showing the merit function as a function of one or more parameters defining the optimization space. The one or more plots can include a two dimensional plot. The two dimensional plot can show the merit function values as a function of sphere. The one or more plots can include a three-dimensional plot. The three dimensional plot can show the merit function values as a function of cylinder and axis.

The representation can be generated based on a measurement of multiple wavefronts indicative of the refractive properties of the eye. Different wavefronts can correspond to different viewing conditions for the eye.

In some embodiments, the method further includes performing additional testing of the eye based on the representation. The additional testing can be performed using an automated phoropter. Alternatively, or additionally, the additional testing can be performed using a head up display.

In another aspect, the invention features an electronic processing system configured to execute the method. Executing the method can include sending data over a network. The electronic processing system can include a computer with a display device and an input device, the computer being configured to execute one or more steps of the method.

In a further aspect, the invention features a computer-readable medium having computer executable instructions for performing the method.

In general, in another aspect, the invention features a system that includes a wavefront aberrometer configured to measure a wavefront indicative of the refractive properties of an eye during operation of the system, a calculation unit configured so that during operation of the system, the calculation unit receives information about the measured wavefront from the wavefront aberrometer and determines a value for a merit function for a plurality of possible prescriptions for the eye, each merit function value corresponding to a visual function of the eye when corrected using the corresponding possible prescription. The system also includes an output device configured so that during operation of the system the output device receives information based on the merit function values and outputs a graphical representation of the merit function values to an eye care professional.

Embodiments of the system can include one or more of the following features and/or features of other aspects. For example, the wavefront aberrometer can be a Hartmann-Shack sensor, a Tscherning aberrometer, a Talbot aberrometer, or double-pass aberrometer. The calculation unit can include an electronic processor and a computer readable medium, the computer readable medium storing instructions that, when executed by the electronic processor, cause the electronic processor to determine the values of the merit function based on information from the wavefront aberrometer. The output device can include an electronic display. In some embodiments, the output device comprises a printer.

Unless otherwise defined, all technical and scientific terms used herein have the same meaning as commonly understood by one of ordinary skill in the art to which this invention belongs. A number of references are incorporated herein by reference. In case of conflict, the present specification will control.

Other features and advantages of the invention will be apparent from the following detailed description.

DETAILED DESCRIPTION

Figure 1B:
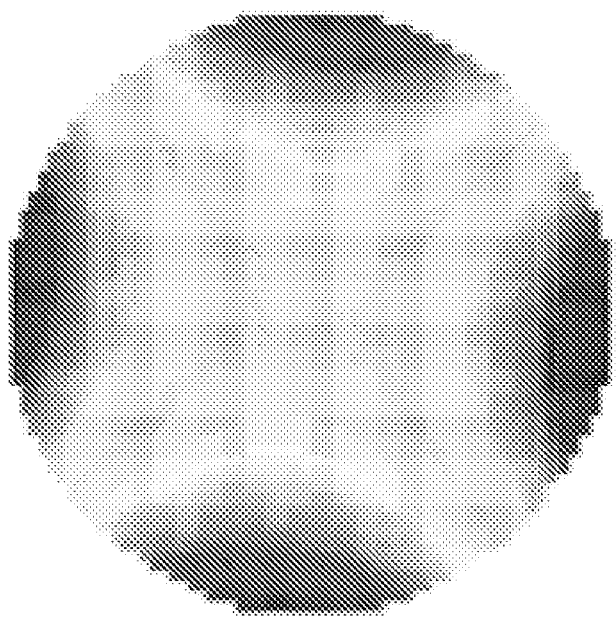
FIG. 1(b) shows a plot of the wavefront shown in FIG. 1(a) where the contributions from higher order aberrations have been filtered out.
Figure 1A:
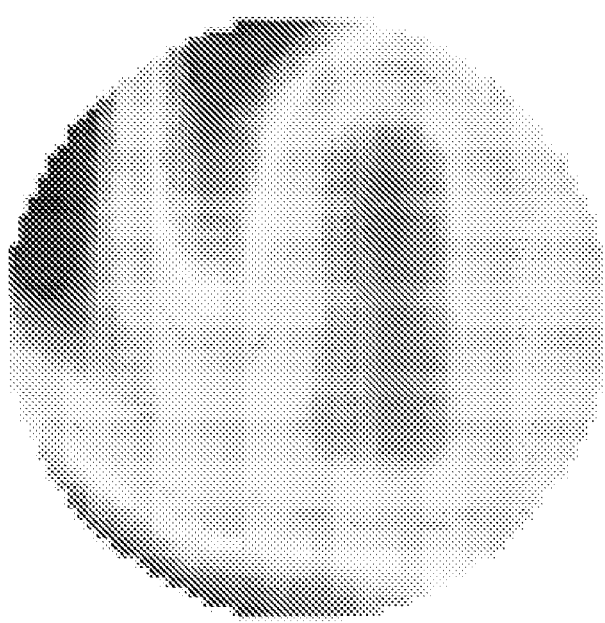
FIG. 1(a) shows a plot of a measured wavefront of an eye.

FIG. 1(a) shows an example of a measured wavefront of a patient's eye. FIG. 1(b) shows the same wavefront where the third and higher order components are filtered out, leaving a "smooth" wavefront. A visual comparison of both pictures makes obvious the difference: in a smooth wavefront, the principal curvatures of the surface are constant over the whole pupil. These curvatures are directly related to refraction, therefore refraction is also constant over the whole pupil. In contrast, in a real eye, refraction is not constant over the pupil, so that rays entering the pupil on different points are refracted differently. Moreover, under different viewing conditions (e.g., bright versus dim lighting environments), the pupil can be different sizes, resulting in differing refractive properties of the eye. Accordingly, when applying a correction to the eye, this correction may be good for some of the pupil areas, but bad for others. In other words, under such conditions a global maximum for a correction is not well defined or easily identifiable, particularly using a manifest refraction.

Conversely, objective methods can identify a global maximum based on a merit function that characterizes the visual acuity of the eye from a measured wavefront. However, purely objective methods don't necessarily account for a variety of subjective factors that may cause an ideal prescription for a patient to deviate from a prescription corresponding to a global maximum of the merit function. Methods that consider both objective and subjective factors are therefore desirable.

In general, methods for determining a prescription for visual aids include evaluating a merit function corresponding to the visual acuity of a patient's eye based on a measurement of a wavefront reflected from the retina. Subsequently, the merit function values are presented to an eye care professional who then identifies the prescription based on those values. The merit function values are presented in a way to easily identify the global maximum, but also allows the eye care professional to assess the visual acuity for prescriptions that are close to, but not at, the global maximum. The eye care professional can then assess, based on other factors, whether a prescription corresponding to the global maximum for visual acuity, or some other prescription, is optimal for the patient.

Referring to FIG. 1, the methods generally include a number of steps, as illustrated by flow chart 100. In a first step, 110, the optical phase error of a patient's eye is measured using an objective method. Typically, this involves measuring a wavefront reflected from the eye using an appropriate sensor. Examples of sensors include various wavefront aberrometers, such as Hartmann-Shack wavefront sensors, Tscherning aberrometers, Talbot aberrometers, and double-pass aberrometers. The functional principal of a wavefront aberrometer is described in DE 601 21 123 T2, which also includes a synopsis of a number of different variants. The entire contents of DE 601 21 123 T2 are incorporated herein by reference.

The measurement data is used as an input for a calculation unit, typically including an electronic processor (e.g., a computer). The calculation unit establishes a multi-dimensional optimization space (step 120), for which the calculation unit calculates a merit function corresponding to the visual acuity of the eye. The dimensions of the optimization space typically correspond to the sphero-cylindrical corrections characterizing an eyeglass prescription (e.g., sphere, cylinder, and axis). The ranges for each of the dimensions of the optimization space can be set by the eye care professional, or preset by the calculation unit. For example, the algorithm for establishing the optimization space can default to a certain range for each dimension, or the default can be over-ridden by the eye care professional based on the professional's experience with the patient. The values for the sphero-cylindrical corrections within each range can be established as desired. For example, the each dimension can include a preset number of values (e.g., 10 or more, 100 or more), so that the incremental change between the values is determined by the range. Alternatively, or additionally, the incremental change between the values can be preset, in which case the number of values for each dimension is determined by setting the range. In some embodiments, the values can correspond to stock lens values within the range in each dimension.

As an example, an optimization space can be established based on the patient's pre-existing prescription, where the ranges for sphere and cylinder are set from −5 D to +5 D about the sphere and cylinder values of the pre-existing prescription. The values can be incremented, by example, by 0.25 D within each range.

Typically, the result is an optimization space that is composed of a finite number of (sphere, cylinder, axis) or (mean power ('M'), J0, J45) co-ordinates for which a merit function can be evaluated.

In some embodiments, the optimization space is composed of a single space. For example, each point in the optimization space can be a three component vector, e.g., having components corresponding to sphere, cylinder and axis or alternatively the Jackson cylinder components (M, J0°, J45°).

In certain embodiments, the optimization space is divided into multiple optimization subspaces, such as two optimization subspaces. For example, each point in the first subspace can be a value for the sphere correction or defocus, and the components of a point in the second subspace can be values for cylinder and axis or the Jackson cylinder components (J0°, J45°).

In a third step, in either case, a surface representing the wavefront of the optical correction for each co-ordinate in the optimization space or subspace is created and subtracted from the original wavefront, which yields a series of corrected wavefronts (step 130).

Then in a fourth step, for each of those wavefronts a merit function is calculated (step 140), which correlates with either visual acuity, contrast sensitivity or with another measure of visual performance, or correlates with a combination of those measures of visual performance.

In a fifth step, 150, the merit function evaluated on the points of the optimization space or subspaces is graphically displayed on an electronic display or printed to a permanent copy. In general, the graphical representation of the merit function values is in a form appropriate for the type of information being displayed. In embodiments, the merit function values are displayed as either two-dimensional plots or three-dimensional plots (e.g., contour plots or three-dimensional surface plots).

In some embodiments, the merit function values can be displayed in a single volume. For example, each point in the volume can have the coordinates (sphere, cylinder, axis, merit function) or (sphere, J0, J45, merit function).

In certain embodiments, the merit function values can be displayed in more than one volume. For example, where the optimization space is divided into two subspaces, then the representation of the merit function can include a graphical display for each of the subspaces. In some embodiments, a two-dimensional plot (e.g., a line graph) can be used for the sphere, where each point in the line is defined in terms of (sphere, merit function). In certain embodiments, a three-dimensional plot (e.g., a contour plot) can be used for the cylinder, where each point in the surface is defined by (cylinder, axis, merit function) or (J0, J45, merit function).

In general, when the optimization space is divided into more than one subspace, the correction for the first substance (e.g., sphere) should be determined first, and then subtracted from the measured wavefront before determining the correction for the second subspace (e.g., cylinder and axis).

Figure 3A:
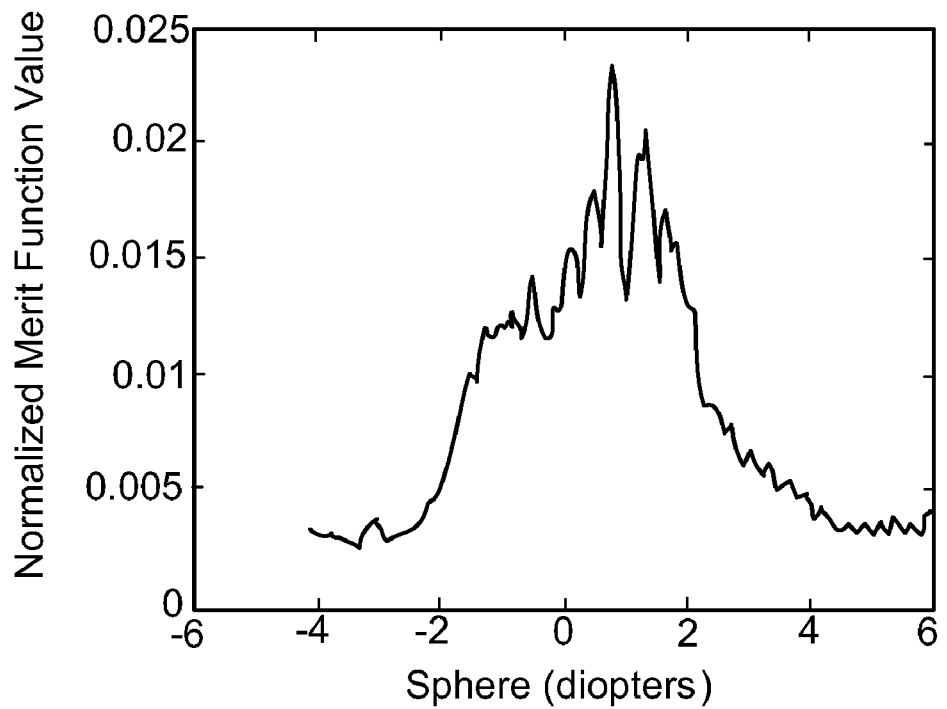
FIG. 3(a) is a plot of merit function values for an optimization space for spherical defocus with constant correction of astigmatism. The plotted values correspond to a merit function for the wavefront measurement shown in FIG. 1(a).
Figure 3B:
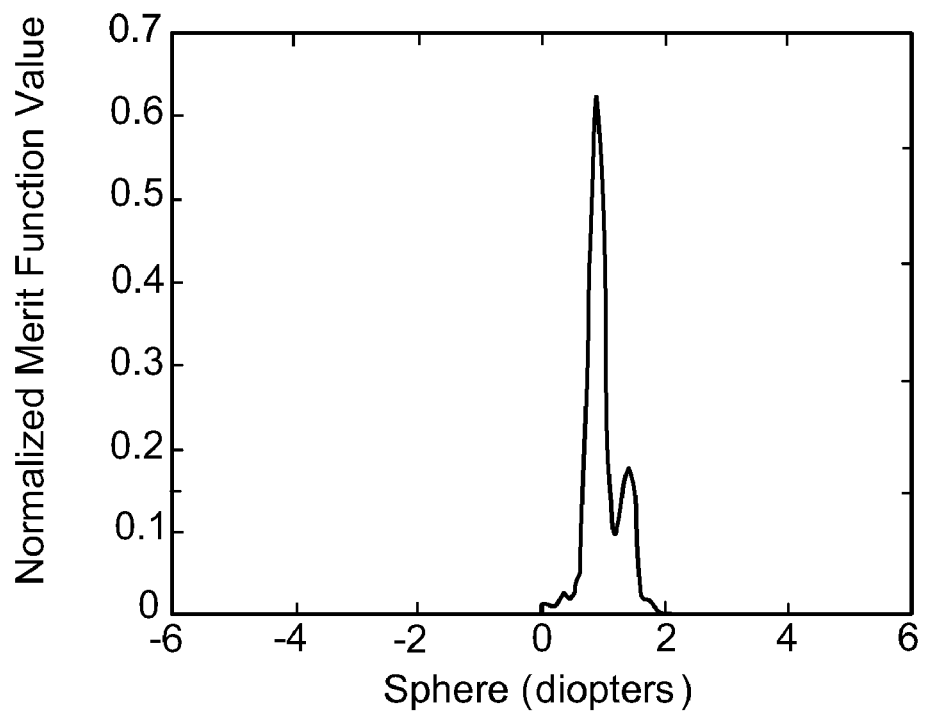
FIG. 3(b) is a plot of merit function values for an optimization space for spherical defocus with constant correction of astigmatism. The plotted values correspond to a merit function for the wavefront measurement shown in FIG. 1(b).

By way of example, FIGS. 3(a) and 3(b) show merit function values in a representation of an optimization space for sphere for the wavefronts shown in FIGS. 1(a) and 1(b), respectively. In order to calculate the data shown in FIGS. 3(a) and 3(b), for each point in the optimization space, a corresponding corrected wavefront was calculated. The corrected wavefront is the measured wavefront corrected by the corresponding spherical correction value. Specifically, in certain embodiments, the corrected wavefront is the original wavefront on which, depending on the point in the optimization space, a spherical surface (here referred to as spherical correction value) is added. The shape of this spherical surface at any radial elongation, r2, is given by the following equation:

$$\text{spherical\_shape} = \text{new\_zernike\_defocus} \times (2 \times r2 - 1),$$

where the new_zernike_defocus is given by $-r0^2 \times [\text{point\_in\_optimspace}]/(4 \times \text{SQRT}(3))$, where r0 is the radius of the pupil belonging to the measured wavefront and [point in optimspace] is the point in the optimization space given in diopters.

Then, a merit function value for each of the resulting corrected wavefronts was calculated. In general, merit function values can be calculated in a variety of ways. In certain embodiments, the merit function is calculated according to the methods disclosed in U.S. patent application Ser. No. 11/840,688, entitled "APPARATUS AND METHOD FOR DETERMINING AN EYEGLASS PRESCRIPTION FOR A VISION DEFECT OF AN EYE," filed on Aug. 17, 2007, the entire contents of which are incorporated herein by reference.

For example, in some embodiments, at least two submetrics can be determined for one of the parameter sets in different stages of the propagation of light through the optical system represented by the eye and an optic corresponding to the eyeglass prescription. In other words, the light passes through the optical system represented by the eye and the optic. One now considers the deviation of the light ray compared to the ideal case, as expressed through a quality metric (submetric), when the light ray has traversed (propagated through) the system represented by the eye and the correction by different travel distances. A propagation in the reverse direction, e.g., directed from the system represented by the eye and the optic towards the object, is likewise conceivable. The propagation being considered here is not tied to a fixed direction through the system represented by the eye and the correction, but can be carried out for any desired number of directions (e.g., in general directions of the line of sight).

These submetrics can include, for example, ray quality metrics such as for example metrics that measure the Strehl ratio or the energy of the point-image wash-out function enclosed within the Airy disc.

An overall metric which reflects in particular the quality of the caustic ("caustic metric") can be determined from a weighted sum of the previously determined submetrics. In some embodiments, all submetrics are given equal weight in the determination of the overall metric (caustic metric). In certain embodiments, a submetric of a preferred propagation stage is weighted more heavily than the submetrics in the propagation stages before and/or behind this preferred propagation stage. If one uses for example submetrics that take the image quality in different planes into account, then the submetric for the image on the retina (which corresponds to the submetric in the preferred propagation stage) would preferably be given more weight than the submetric for an image before or behind the retina of the eye. The weight ratio could be for example 60/40.

The y-axes in the plots shown in FIGS. 3(a) and 3(b) display the merit function value for the different corrected wavefronts. As evident from the figures, for a smooth wavefront (e.g., as shown in FIG. 3(b)) there is a clear maximum. As evident in FIG. 3(a), however, for the wavefront that includes higher order aberrations, there are several local maxima which are relatively close to the global maximum.

Figure 4A:
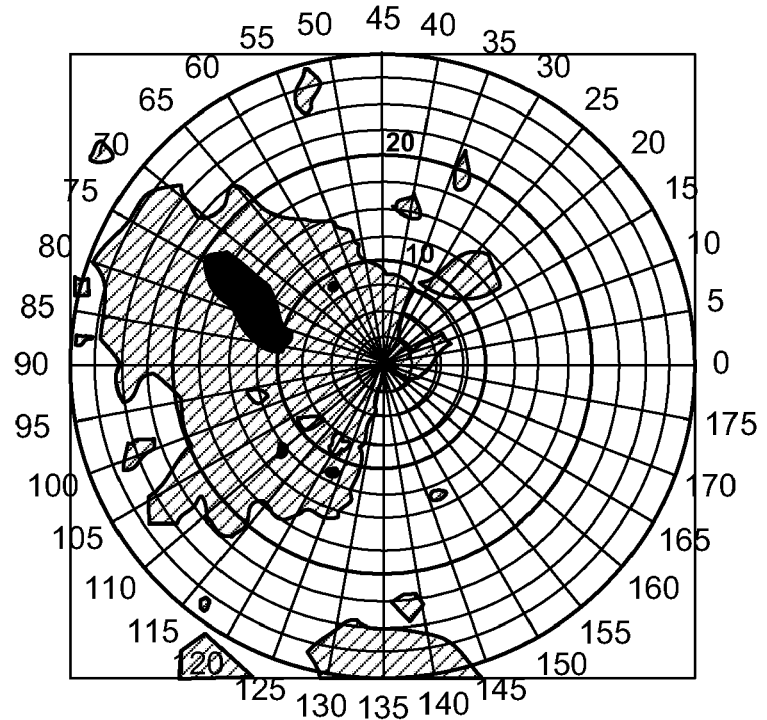
FIG. 4(a) is a plot of merit function values for an optimization space for cylinder and axis with a mean power error of zero. The plotted values correspond to a merit function for the wavefront measurement shown in FIG. 1(a).
Figure 4B:
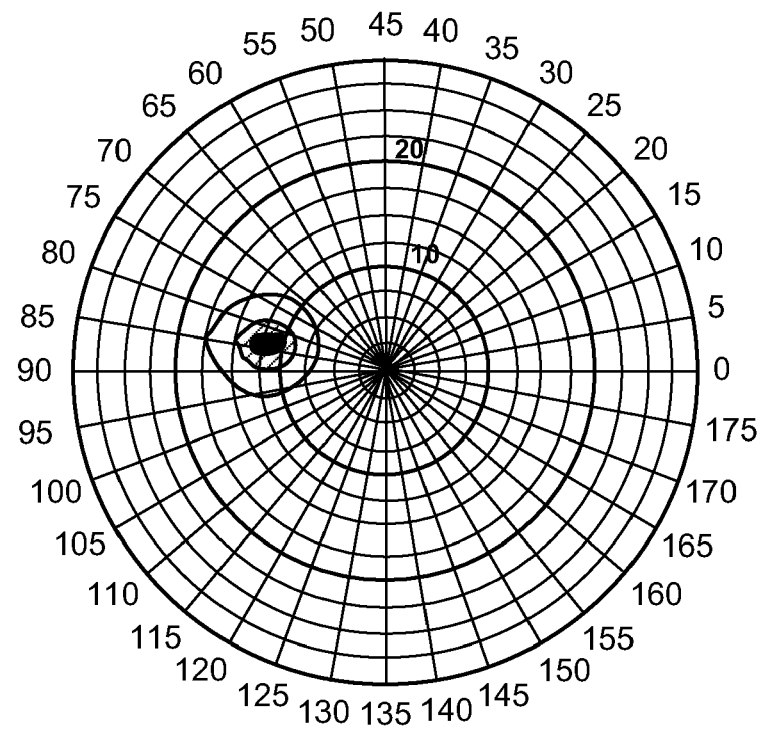
FIG. 4(b) is a plot of merit function values for an optimization space for cylinder and axis with a mean power error of zero. The plotted values correspond to a merit function for the wavefront measurement shown in FIG. 1(b).

Also the optimization space for cylinder changes dramatically in presence of higher order aberrations. FIGS. 4(a) and 4(b) show the merit function values in an optimization space for cylinder and cylinder axis for the wavefronts shown in FIGS. 1(a) and 1(b), respectively. The graphs were calculated is a similar way as described above for the spherical correction: first the mean sphere of the measured wavefronts was corrected. Thereafter, corrected wavefronts for the different cross-cylinder corrections were calculated. Finally, merit function values were evaluated from the corrected wavefronts. The merit function values are displayed as contours in the polar plots. The colours are the contour lines at 0.1, 0.25, 0.50, 0.75 and 0.95 of the normalized maximum value of the merit function. The values of the cross-cylinder were calculated in form of amplitude and axis and displayed in polar coordinates. As evident by comparison of FIGS. 4(a) and 4(b), the contours of the merit function values in presence of higher order aberrations (FIG. 4(a)) is highly irregular compared to the merit function values for a smooth wavefront (FIG. 4(b)).

Figure 2:
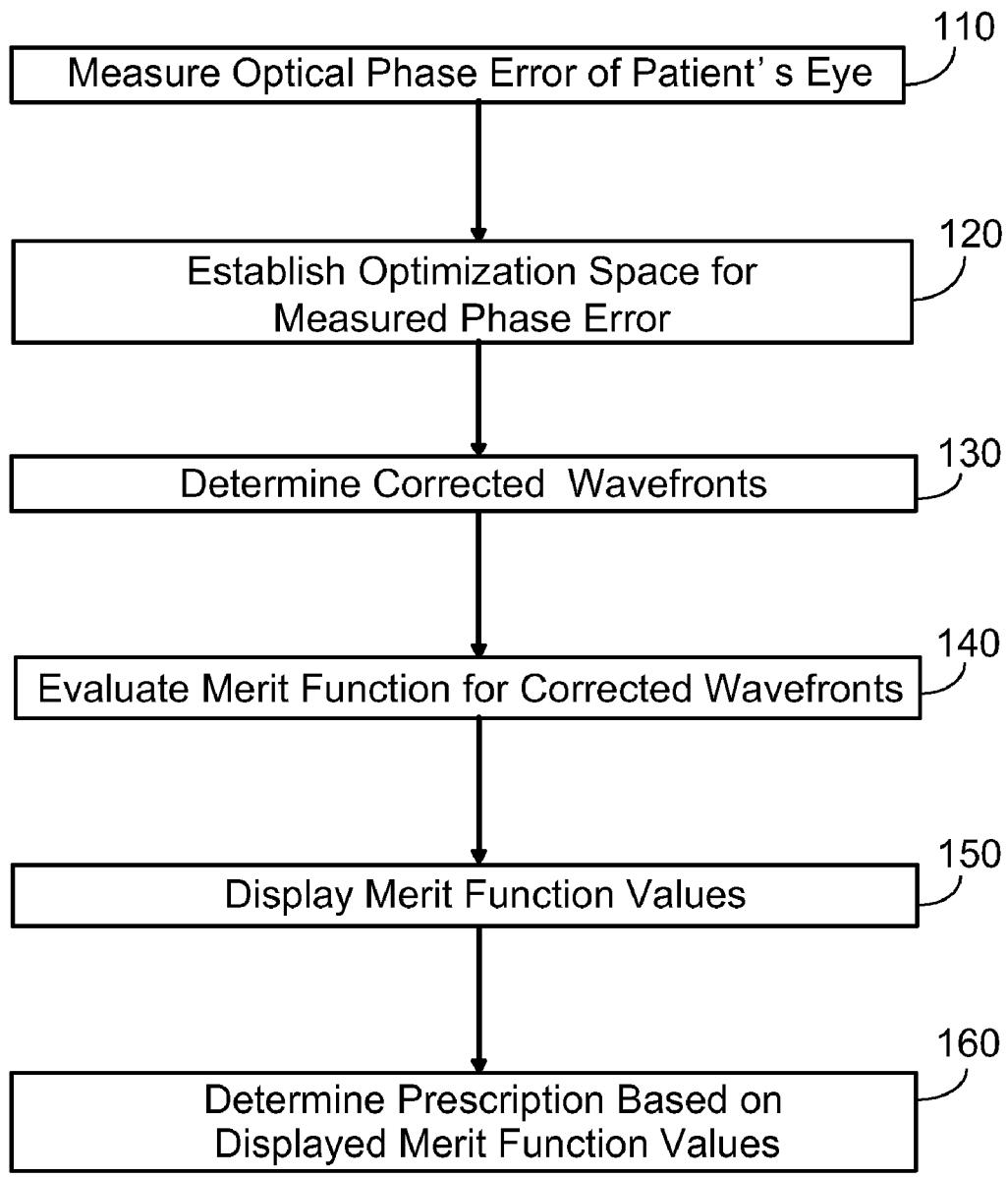
FIG. 2 is a flow chart showing steps in a method for determining a prescription for visual aids.

Referring again to FIG. 2, in a sixth step, the eye care professional uses the graphical representations of the merit function as a guide for finally determining the prescription for the patient (step 160). Generally, the eye care professional will determine the prescription based not only on the merit function values, but on other factors as well. For example, the eye care professional will consider factors such as the patient's existing prescription, viewing conditions in which the prescribed visual aids are likely to be used (e.g., bright conditions, dim conditions) and/or other factors.

In general, in additional to displaying the merit function values, the graphical representation can provide additional information to the eye care professional as well. For example, in some embodiments, the representation includes a suggestion for a preferred correction, e.g., in the form of (sphere, cylinder and axis) or (M, J0, J45). The suggestion can correspond to the largest merit function value or to some other value.

As another example, in some embodiments, the range of corrections within the boundaries where blur starts to be just noticeable can be shown. Alternatively or additionally, the calculation unit can show a number of different suggested corrections, all of them being within the boundaries where blur starts to be just noticeable. The coordinates of such a blur boundary can be based, for example, on psychometric functions of the 'just noticeable difference' (JND) for blur as it correlates to the type of metric being plotted; such a function being derived experimentally for each type of metric. Alternatively, or additionally, the coordinates of the blur boundary can be determined by experimentally-derived psychometric functions for suprathreshold blur perception defined by subjective criteria such as 'objectionable blur' or 'troublesome blur'.

In some embodiments, the calculation unit preselects and displays suggested corrections that are within the boundaries where blur starts to be just noticeable, and which might be preferred based on other factors. For example, the calculation unit can display a correction having a small value for cylinder, a correction having the cylinder axis closest to 0° or 90°, a correction having the most plus mean spherical power, a correction corresponding to a relatively light ophthalmic lens, a correction giving a relatively small distortion on a particular ophthalmic lens design, a correction corresponding to a small ablation depth in the case the prescription is going to be used for refractive surgery, a correction being the closest to certain pre-established values (e.g. corresponding to stock lenses, intraocular lenses, or other lenses), and/or a correction corresponding to a combination of the above mentioned criteria and/or other criteria.

In some embodiments, the merit function is evaluated for multiple wavefront measurements of the same eye. For example, the wavefronts from the eye can be measured a number of times under differing conditions. The different conditions can correspond to different pupil sizes or reference object vergences corresponding to a range of viewing distances. For example, daylight conditions would correspond to a smaller pupil while dim light conditions would correspond to a larger pupil. As another example, the wavefront measurements can be made while the subject accommodates to a series of different accommodative stimuli that correspond to different viewing distances. Subsequently, the eye care professional can consider the different conditions when finalizing the patient's prescription.

In certain embodiments, output from the calculation unit can be used to guide additional testing of the patient. For example, the calculation unit can direct suggested corrections to an automated phoropter, which automatically sets up to this correction for testing on the patient. In some embodiments, the calculation unit provides output in the form of a set of suggested corrections to an automated phoropter which consecutively sets the corrections so that the patient can decide subjectively by looking, e.g., on a test chart or on a target to test near vision which one of those corrections they prefer.

Other implementations are also possible. For example, in some embodiments, the calculation unit provides output to a head mounted display which uses active optics to set the corrections in a similar way a phoropter would, but allows a more natural testing condition for the patient by conducting different visual tasks (e.g., reading, observing a computer screen or television, observing objects at a distance). The head mounted display can simulate not only the suggested prescription of, e.g., sphere, cylinder, and axis, but also the optical design of the lens the patient is going to wear later, e.g., a progressive glass.

In some embodiments, the wavefront sensor and the calculation unit are integrated together with the phoropter or the head mounted display, respectively. Integration of the different units can improve workflow in the prescription determination process. As an example, the patient can look through the phoropter to a suitable object on infinity, while a measurement of the wavefront takes place. Next, the merit function over an optimization space or subspaces is calculated and graphically displayed to the eye care professional and a first suggested correction automatically set in the phoropter or head mounted display. The eye care professional then navigates through different suggested corrections so that the patient can confirm them subjectively.

The eye chart can be connected to the phoropter so that it automatically displays the appropriate test target or optotype for the suggested correction, e.g., the size of the optotype or a specific target that has been optimized to detect subtle errors of vision. It can be advantageous where the display of the optimization space, the phoropter and eye chart are controlled from a single interface, for instance, in a touch screen panel or computer display and keyboard. This control interface can be integrated with the calculation unit and/or phoropter or head mounted display.

While the foregoing discussion refers to implementations for correcting up to second order aberrations, in general, the invention is not limited to second order aberrations. For example, in some embodiments, the methods can be expanded to allow refraction using higher order aberrations. In such cases, the optimization space is expanded by one or more additional dimensions, e.g., for higher order aberrations, such as spherical aberration and/or coma. Such a higher order refraction can then be used by the eyecare professional to specify an ophthalmic correction that includes higher order correction by altering the phase of the incident wavefront in the plane of the pupil according to the prescribed higher order aberration correction.

Furthermore, while the embodiments discussed above are in reference eye glass visual aids, in general, the techniques can be applied to determining a prescription for contact lenses or refractive surgery as well.

A number of embodiments have been described. Other embodiments are in the claims.

What is claimed is:

1. A system, comprising:
   a wavefront aberrometer configured to measure a wavefront indicative of the refractive properties of an eye during operation of the system;
   a calculation unit configured so that during operation of the system, the calculation unit receives information about the measured wavefront from the wavefront aberrometer and determines a value for a merit function for a plurality of possible prescriptions for the eye, each merit function value corresponding to a visual function of the eye when corrected using the corresponding possible prescription; and
   an output device configured so that during operation of the system, the output device receives information based on the merit function values and outputs a graphical representation of the merit function values to an eye care professional.

2. The system of claim 1, wherein the wavefront aberrometer is a Hartmann-Shack sensor, a Tscherning aberrometer, a Talbot aberrometer, or double-pass aberrometer.

3. The system of claim 1, wherein the calculation unit comprises an electronic processor and a computer readable medium, the computer readable medium storing instructions that, when executed by the electronic processor, cause the electronic processor to determine the values of the merit function based on information from the wavefront aberrometer.

4. The system of claim 1, wherein the output device comprises an electronic display.

5. The system of claim 1, wherein the output device comprises a printer.

6. The system of claim 1, wherein the graphical representation is a two-dimensional plot.

7. The system of claim 1, wherein the graphical representation is a three-dimensional plot.

8. The system of claim 1, wherein the graphical representation is a contour plot.

9. The system of claim 1, wherein the graphical representation is a three-dimensional surface plot.

10. The system of claim 1, wherein the graphical representation further includes a suggestion for a preferred correction.

11. The system of claim 10, wherein the suggestion for the preferred correction includes information about sphere.

12. The system of claim 11, wherein the suggestion for the preferred correction includes information about cylinder.

13. The system of claim 12, wherein the suggestion for the preferred correction includes information about axis.

14. The system of claim 10, wherein the suggestion for the preferred correction includes information about cylinder.

15. The system of claim 14, wherein the suggestion for the preferred correction includes information about axis.

16. The system of claim 10, wherein the suggestion for the preferred correction includes information about axis.

17. The system of claim 10, wherein the suggestion for the preferred correction is in the form of (sphere, cylinder, axis).

18. The system of claim 10, wherein the suggestion for the preferred correction is in the form of (M, J0, J45).

19. The system of claim 10, wherein the suggestion for the preferred correction is a largest merit function.

20. The system of claim 1, wherein the graphical representation is configured so that the eye care professional can identify a prescription corresponding to a maximum merit function value from the representation.

21. The system of claim 1, wherein the graphical representation is configured so that the eye care professional can identify one or more prescriptions corresponding to prescriptions at which vision becomes blurred.

22. The system of claim 1, wherein the graphical representation comprises one or more plots showing the merit function as a function of one or more parameters defining an optimization space.

23. The system of claim 22, wherein the one or more plots comprises a two dimensional plot.

24. The system of claim 23, wherein the two dimensional plot shows the merit function values as a function of sphere.

25. The system of claim 22, wherein the one or more plots comprises a three-dimensional plot.

26. The system of claim 25, wherein the three dimensional plot shows the merit function values as a function of cylinder and axis.

27. The system of claim 1, wherein the graphical representation is generated based on a measurement of multiple wavefronts indicative of the refractive properties of the eye.

* * * * *

UNITED STATES PATENT AND TRADEMARK OFFICE
CERTIFICATE OF CORRECTION

PATENT NO.        : 8,007,103 B2
APPLICATION NO.   : 12/192463
DATED             : August 30, 2011
INVENTOR(S)       : Michael Morris et al.

It is certified that error appears in the above-identified patent and that said Letters Patent is hereby corrected as shown below:

Column 2,
Line 46, delete "The or" and insert --The one or--

Column 2,
Line 49, delete "sub-spaces" and insert --sub-spaces.--

Signed and Sealed this
Twenty-fifth Day of October, 2011

David J. Kappos
*Director of the United States Patent and Trademark Office*